United States Patent
Plakogiannis et al.

(10) Patent No.: US 9,757,374 B2
(45) Date of Patent: *Sep. 12, 2017

(54) ARIPIPRAZOLE COMPOSITIONS AND METHODS FOR ITS TRANSDERMAL DELIVERY

(71) Applicant: Aequus Pharmaceuticals Inc., Vancouver (CA)

(72) Inventors: Fotios M. Plakogiannis, Whitestone, NY (US); Muhammed Anwar Hossain, Congers, NY (US)

(73) Assignee: Aequus Pharmaceuticals Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/825,318

(22) Filed: Aug. 13, 2015

(65) Prior Publication Data

US 2015/0342949 A1    Dec. 3, 2015

Related U.S. Application Data

(63) Continuation-in-part of application No. 13/879,485, filed as application No. PCT/US2011/057080 on Oct. 20, 2011, now Pat. No. 9,138,402.

(60) Provisional application No. 61/407,591, filed on Oct. 28, 2010.

(51) Int. Cl.
*A61K 31/496* (2006.01)
*A61K 9/00* (2006.01)

(52) U.S. Cl.
CPC .......... *A61K 31/496* (2013.01); *A61K 9/0014* (2013.01)

(58) Field of Classification Search
CPC ........................... A61K 31/496; A61K 9/0014
See application file for complete search history.

(56) References Cited

U.S. PATENT DOCUMENTS

| | | | |
|---|---|---|---|
| 5,558,071 A | 9/1996 | Ward et al. | |
| 6,579,581 B2 | 6/2003 | Bartz et al. | |
| 7,807,680 B2 * | 10/2010 | Kostanski ............ | A61K 9/0019 514/252.1 |
| 8,461,129 B2 | 6/2013 | Bolduc et al. | |
| 2004/0170672 A1 * | 9/2004 | Selzer .................. | A61K 31/496 424/449 |
| 2007/0032651 A1 | 2/2007 | Salama et al. | |
| 2008/0112986 A1 | 5/2008 | Kostanski et al. | |
| 2009/0156813 A1 | 6/2009 | Aronhime et al. | |
| 2010/0015195 A1 | 1/2010 | Jain et al. | |
| 2011/0028412 A1 | 2/2011 | Cappello et al. | |
| 2012/0184563 A1 | 7/2012 | Hanma | |
| 2013/0041004 A1 | 2/2013 | Drager et al. | |
| 2013/0084243 A1 | 4/2013 | Goetsch et al. | |
| 2013/0096073 A1 | 4/2013 | Sidelman | |

FOREIGN PATENT DOCUMENTS

| | | | |
|---|---|---|---|
| CA | 2816203 A1 | | 5/2012 |
| CN | 101401783 | * | 9/2007 |
| EP | 0564307 A1 | | 6/1993 |
| WO | 2009060473 A2 | | 5/2009 |

OTHER PUBLICATIONS

Paudel et al. (Ther. Deliv. Jul. 2010, 1 (1), 109-131).*
Pathan et al. (Trop. J. Pharm. Res. 2009, 8 (2), 173-179).*
Lubrizol (TDS-730, available Nov. 24, 2009).*
International Search Report for PCT/US2011/057080.
Lubizol, TDS-730 "Viscosity of Carbopol Polymers in Aqueous Systems" Published Nov. 24, 2009.
NMP-MSD for n-methylpyrrolidone. (http://www3.imperial.ac.uk.pls/portallive/docs/1/7276131.PDF), May, 2001.
Bhattacharjee, H: Thoma, L. "Parenteral drug administration: routes of administration and devices" Pharmaceutical Dosage Forms: Parenteral Medications, Third Edition, Chapter 2, Aug. 2010, pp. 7-29.
Paudel, K.S. et al. "challenges and opportunities in dermal/transdermal delivery" Ther. Deliv. Jul. 2010, 1(1), 109-131.
Baranda, L. et al. "correlation between pH and irritant effect of cleansers marketed for dry skin" Int. J. Derm. 2002, 41, 494-499.
Pathan, I.B.: Setty, C.M. "chemical Penetration Enhancers for Transdermal Drug Delivery Systems" Trop. J. Pharm. Res. 2009, 8 (2) 173-179.
www.atitesting.com/atinextgen/skillsmodules/content/medication-administration1/equipment/routes.html; Retrieved Jan. 27, 2015.
Pirot, et al., Proc. Natl. Acad. Sci. vol. 94, pp. 1562-1567, Feb. 1997.
UNC. "The Pharmaceutics and Compounding Laboratory" (http://pharmlabs,unc.edu/labs/gels/agents.htm) accessed Aug. 5, 2014.
Inque, et al. Effects of the Novel Antipsychotic Agent 7-[4-2,3-dichlorophenyl)-1-piperazinyl]butyloxyl-3,4-dihydro-2 (1H)-quinolinone (OPC-14597) on Prolactin Release from the Rat anterior Pituitary Gland, the Journal of Pharmacology and Experimental Therapeutics, 1996, 277(1):137-143.
Burris, et al. Aripiprazole is a High Affinity Partial Agonist at Human D2 Dopamine receptors, Int. J. Neuropsychopharmacol, 2003;3(Suppli.1), S129.
Petrie, et al. Aripiprazole, a new typical antipsychotic: Phase 2 clinical trial result, Eur. Neuropsychopharm 1997;7 (suppl 2) S227.
Saha, et al, Efficacy and safety of Aripiprazole and risperidone vs. Placebo in patients with schizophrenia and schizoaffective disorder, World J. Biol Psych 2001; 2 (suppl 1) 305S.
Getta , A., Psychotropic Drugs and transdermal Delivery: An overview, International Juornal of Pharma and bio Science, 2001: V1(2)2010.
International Search Report for PCT/IB2016/054826 mailed Nov. 28, 2016.

* cited by examiner

*Primary Examiner* — Snigdha Maewall

(74) *Attorney, Agent, or Firm* — Caesar Rivise, PC

(57) ABSTRACT

The present invention discloses compositions of liquid and gel formulation containing aripiprazole in the form of a patch for transdermal delivery.

16 Claims, 3 Drawing Sheets

ARIPIPRAZOLE COMPOSITIONS AND METHODS FOR ITS TRANSDERMAL DELIVERY

FIELD OF THE INVENTION

The present invention relates to the field of transdermal delivery of pharmaceutical compositions, which have an acceptable in vitro performance and good bioavailability. In particular, the transdermal pharmaceutical compositions of the present invention include liquids or gels of aripiprazole in a patch dosage form.

BACKGROUND OF INVENTION

Aripiprazole (ARPZ) is the first of a new class of atypical antipsychotics (third generation). Biochemically, ARPZ is a partial agonist of the D2 family of dopamine receptors.[1,2] It is active against positive and negative symptoms of schizophrenia.[3,4]

ARPZ is a quinolinone derivative, white crystalline powder, practically insoluble in water, with a low melting point (135-140° C.), MW 448.38 g/mole and partition coefficient of 4.54.

BRIEF SUMMARY OF THE INVENTION

The invention provides a pharmaceutical composition comprising aripiprazole in a dosage form for transdermal delivery comprising aripiprazole about 7%, Carbopol about 5%, DMSO about 40%, Ethanol about 25%, Lactic acid about 5%, N-methyl-2-pyrrolidone (NMP) about 1.75%, Oleic acid about 4%, propylene glycol (PG) about 7.25%, and q.s. water. The invention provides a pharmaceutical composition wherein the aripiprazole is in a gel or liquid form. The invention provides a pharmaceutical composition wherein the pH of the composition is approximately 6 to 7.

The invention provides a pharmaceutical composition pharmaceutical composition comprising aripiprazole in a dosage form for transdermal delivery comprising aripiprazole about 7%, Klucel (hydroxypropylcellulose (HPC)) about 2%, DMSO about 40%, Ethanol about 25%, Lactic acid about 5%, N-methyl-2-pyrrolidone (NMP) about 1.75%, Oleic acid about 4%, propylene glycol about 10.25%, and q.s. water. The invention provides a pharmaceutical composition wherein the aripiprazole is in a gel or liquid form. The invention provides a pharmaceutical composition wherein the pH of the composition is approximately 6 to 7.

The invention provides a pharmaceutical composition pharmaceutical composition comprising aripiprazole in a dosage form for transdermal delivery comprising about aripiprazole about 7%, Klucel (hydroxypropylcellulose (HPC)) about 4%, DMSO about 5%, Ethanol about 5%, isopropyl myristate (IPM) about 1.5%, Oleic acid about 23%, Lactic acid about 6%, PG about 23.5%, Polyethylene glycol (PEG)—20%, and Glycerin about 5%. The invention provides a pharmaceutical composition wherein the aripiprazole is in a gel or liquid form. The invention provides a pharmaceutical composition wherein the pH of the composition is approximately 6 to 7.

The invention provides a pharmaceutical composition pharmaceutical composition comprising aripiprazole in a dosage form for transdermal delivery comprising about aripiprazole about 7%, DMSO about 40%, N-methyl-2-pyrrolidone (NMP) about 1.75%, propylene glycol (PG)—10.25%, Ethanol about 16%, Lactic acid about 5%, Terpineol about 10%, Oleic acid about 2%, Water about 5%, and Carbopol about 3%. The invention provides a pharmaceutical composition wherein the aripiprazole is in a gel or liquid form. The invention provides a pharmaceutical composition wherein the pH of the composition is approximately 6 to 7.

The invention provides a pharmaceutical composition pharmaceutical composition comprising aripiprazole in a dosage form for transdermal delivery comprising aripiprazole about 7%, DMSO about 40%, N-methyl-2-pyrrolidone (NMP) about 1.75%, propylene glycol (PG) about 9.25%, Ethanol about 25%, Lactic acid about 5%, Oleyl alcohol about 4%, Water about 5%, and Carbopol about 3%. The invention provides a pharmaceutical composition wherein the aripiprazole is in a gel or liquid form. The invention provides a pharmaceutical composition wherein the pH of the composition is approximately 6 to 7.

The invention provides a method of treating schizophrenia in patient in need of such treatment comprising: selecting a patient in need of treatment for schizophrenia; administering the pharmaceutical composition of the invention, thereby treating schizophrenia. The invention provides for the use of a pharmaceutical composition of the invention to manufacture a medicament for treating, for example, schizophrenia.

BRIEF DESCRIPTION OF SEVERAL VIEWS OF THE DRAWINGS

The invention will be described in conjunction with the following drawings wherein.

DETAILED DESCRIPTION OF THE INVENTION

Figure 1:
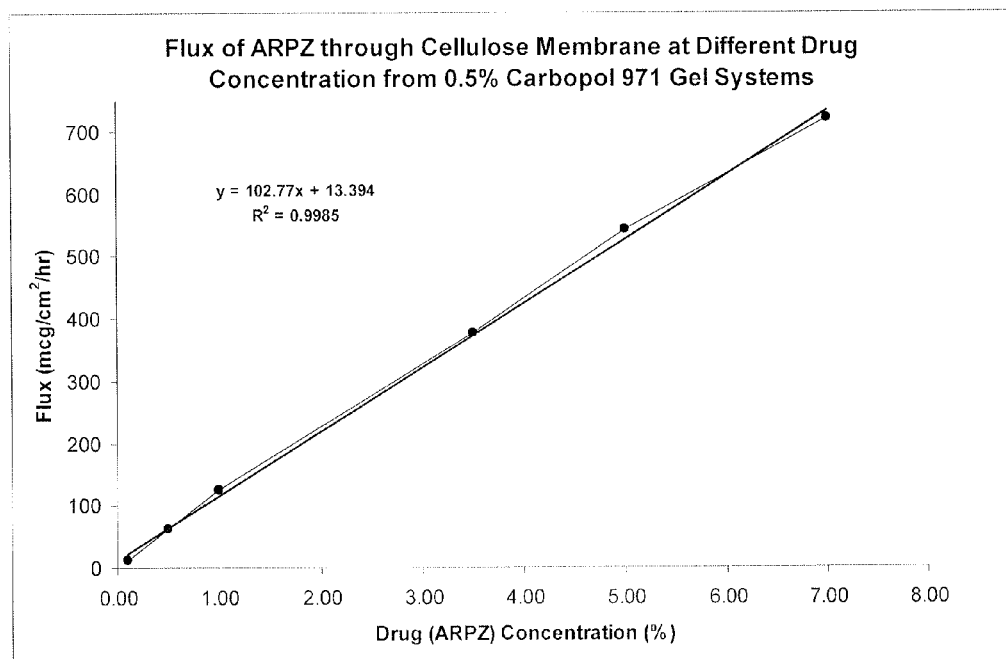
FIG. 1 is a chart showing the Effect of Drug Concentration on the Flux of ARPZ through Cellulose Membrane from 0.5% Carbopol 971 Gel Systems.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "agent" refers to any molecule, compound, methodology and/or substance for use in the prevention, treatment, management and/or diagnosis of a disease or condition. As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for the purpose of treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, such as cancer, and/or the amelioration of one or more symptoms thereof resulting from the administration of one or more therapies.

The term "derivative" or "derivatized" as used herein includes chemical modification of a compound of the invention, or pharmaceutically acceptable salts thereof or mixtures thereof. That is, a "derivative" may be a functional equivalent of a compound of the invention, which is capable of inducing the improved pharmacological functional activity in a given subject. Illustrative of such chemical modifications would be replacement of hydrogen by a halo group, an alkyl group, an acyl group or an amino group.

As used herein, the term "pharmaceutically acceptable salts" includes acid addition salts or addition salts of free bases. The term "pharmaceutically acceptable salts" of a compound of the invention is also meant to include within its scope all the possible isomers and their mixtures, and any pharmaceutically acceptable metabolite, bioprecursor and/or pro-drug, such as, for example, a compound which has a structural formula different from the one of the compounds of the invention, and yet is directly or indirectly converted in vivo into a compound of the invention, upon administration to a subject, such as a mammal, particularly a human being.

The compound may be in the form of a pharmaceutically acceptable salt, such as an acid addition salt or a base salt, or a solvate thereof, including a hydrate thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts.

The invention provides a pharmaceutical composition comprising aripiprazole in a dosage form for transdermal delivery. The invention provides a pharmaceutical composition of the invention wherein the aripiprazole is in a gel or liquid form. The invention provides a pharmaceutical composition of the invention wherein the aripiprazole is present in the amount of 1 to 20% w/v. The invention provides a pharmaceutical composition of the invention wherein the aripiprazole is present in the amount of 1 to 20% w/v. The invention provides a pharmaceutical composition of the invention wherein the gel contains a gelling agent in the range of about 0.1% to 5% w/v. The invention provides a pharmaceutical composition of the invention further comprising approximately 40% N-methyl-2-pyrrolidone, 40% Dimethylsulfoxide, 15% alcohol and 5% water.

The invention provides a pharmaceutical composition for transdermal delivery which comprises ARPZ 2%; DMSO at a concentration of about 10 to 40%, and at a preferred concentration of about 25%; NMP at a concentration of about 5 to 40%, and a preferred concentration is about 10%; Isopropyl alcohol (IPA) at a concentration of about 1 to 15%, and a preferred concentration is about 5%; Ethyl Alcohol at a concentration of about 15 to 40%, and a preferred concentration is about 40%; PEG 400 at a concentration of about 1 to 15%, and a preferred concentration is about 15%; CARBOPOL® 971P at a concentration of about 0.25 to 5%, and a preferred concentration is about 0.5%; and water, q.s. to 100%.

The invention provides a pharmaceutical composition of the invention being in the form of a liquid and comprising an alcohol, glycol, mineral oil, and/or vegetable oil. The invention provides a pharmaceutical composition of the invention wherein the composition is in a gel form and further comprises a gelling agent selected from the group consisting of natural polymers, semisynthetic polymers, synthetic polymers, carboxyvinyl polymers or carbomers, CARBOPOL® 940, CARBOPOL® 934, CARBOPOL® 971, poloxamer, polyacrylamide, polyvinyl alcohol, polyethylene and co-polymers thereof. The invention provides a pharmaceutical composition of the invention wherein the form is a patch for transdermal delivery. The invention provides a pharmaceutical composition of the invention being in the dosage form of an ointment, cream, emulsion, or liposome. The invention provides a pharmaceutical composition of the invention wherein the aripiprazole is present in the amount of 1 to 20% w/v.

The invention provides a pharmaceutical composition of the invention further comprising an enhancer. The invention provides a pharmaceutical composition of the invention wherein the enhancer is selected from the group consisting of lauric acid, myristic acid, water, sulfoxides, dimethylsulfoxide, dimethylacetamide, dimethylformamide, decymethylsulfoxide, pyrrolidones, fatty acid esters, fatty acids, alcohols, fatty alcohols and glycols, urea, essential oils, terpene and terpenoids, liposomes, niosomes, transferomes and ethanosomes.

The invention provides a pharmaceutical composition of the invention wherein the pH of the composition is maintained at approximately 6 to 7. The invention provides a pharmaceutical composition of the invention wherein the pH of the composition is maintained at approximately 6 to 7.

In an exemplary embodiment, the invention provides a pharmaceutical composition comprising about ARPZ—7%, Carbopol—5%, DMSO—40%, Ethanol—25%, Lactic acid—5%, N-methyl-2-pyrrolidone (NMP)—1.75%, Oleic acid—4%, propylene glycol (PG)—7.25%, and q.s. Water (ca. 5%).

In an exemplary embodiment, the invention provides a pharmaceutical composition comprising about ARPZ—7%, Klucel (hydroxypropylcellulose (HPC))—2%, DMSO—40%, Ethanol—25%, Lactic acid—5%, N-methyl-2-pyrrolidone (NMP)—1.75%, Oleic acid—4%, propylene glycol—10.25%, and q.s. Water (ca. 5%).

In an exemplary embodiment, the invention provides a pharmaceutical composition comprising about ARPZ—7%, Klucel (hydroxypropylcellulose (HPC))—4%, DMSO—5%, Ethanol—5%, isopropyl myristate (IPM)—1.5%, Oleic acid—23%, Lactic acid—6%, PG—23.5%, Polyethylene glycol (PEG)—20%, and Glycerin—5%.

In an exemplary embodiment, the invention provides a pharmaceutical composition comprising about ARPZ—7%, DMSO—40%, N-methyl-2-pyrrolidone (NMP)—1.75%, propylene glycol (PG)—10.25%, Ethanol—16%, Lactic acid—5%, Terpineol—10%, Oleic acid—2%, Water—5%, and Carbopol—3%.

In an exemplary embodiment, the invention provides a pharmaceutical composition comprising about ARPZ—7%, DMSO—40%, N-methyl-2-pyrrolidone (NMP)—1.75%, propylene glycol (PG)—9.25%, Ethanol—25%, Lactic acid—5%, Oleyl alcohol—4%, Water—5%, and Carbopol—3%.

Preparation of suitable formulations is within the skill of those in the art, and suitable excipients for inclusion in any such formulation include, for example, gellants, viscosifiers, penetration enhancers, preservatives, such as antibiotics and antifungals, and cosmetic ingredients, such as scents and colorings.

Suitable preservatives will be apparent to those skilled in the art, and include the parabens (methyl, ethyl, propyl and butyl), benzoic acid and benzyl alcohol. Preservatives employed solely for that purpose will generally form 1% (w/w) or less of the final topical formulation.

Pharmaceutical compositions of the present invention can include nanoparticles, composite nanoparticles, nanosuspension, or nanocapsules of the present invention The invention will be illustrated in more detail with reference to the following Examples, but it should be understood that the present invention is not deemed to be limited thereto.

Example 1

ARPZ is practically insoluble in water and has been formulated as a liquid and gel dosage form (Table 1). All reported values are in weight/volume percentage (W/V)

TABLE 1

Composition of liquid and gel formulation of Aripiprazole (5% W/V)

|  | W/V | W/V |
| --- | --- | --- |
| N-methyl-2-pyrrolidone (NMP) | 40% | 40% |
| Dimethyl Sulfoxide (DMSO) | 40% | 40% |
| Ethyl Alcohol | 15% | 15% |
| Carbopol 971P | — | 0.5% |
| Water | 5% | 4.5% |
| Total | 100.00% | 100.00% |

An optimal mixture design of experiments was used to select the levels of the formulation variables. The optimum composition of a 1% W/V to 20% W/V ARPZ liquid formulation was predicted to have NMP 40%, DMSO 40%, Alcohol 15% and water 5% (Table 1). The gel formulation should contain a gelling agent in the range of about 0.1% to 5% W/V and the optimum APRZ composition should range from about 1% W/V to 20% W/V with about 0.5% W/V of the gelling agent. Therefore, the gel formulation was predicted to have a NMP of 40%, DMSO 40%, Alcohol 15%, Carbopol 971 0.5%, and Water 4.5% (Table 1). However, Table 2 lists other combinations that also could produce successful liquid and gel ARPZ formulations in accordance with the present invention.

TABLE 2

Concentration Ranges of N-Methyl-2-Pyrolidone (NMP), Dimethl Sulfoxide (DMSO), Ethyl Alcohol, and Water in Liquid Aripiprazole Formulation

| Formulation | NMP | DMSO | Alcohol | Water |
| --- | --- | --- | --- | --- |
| 1. | 50 | 50 | — | — |
| 2. | 40 | 40 | 20 | — |
| 3. | 40 | 40 | — | 20 |
| 4. | 40 | 40 | 15 | 5 |
| 5. | 40 | 40 | 10 | 10 |
| 6. | 40 | 40 | 5 | 15 |
| 7. | 30 | 30 | 20 | 20 |
| 8. | 30 | 30 | 30 | 10 |
| 9. | 30 | 40 | 25 | 5 |
| 10. | 40 | 30 | 25 | 5 |
| 11. | 45 | 45 | 10 | 0 |
| 12. | 45 | 40 | 10 | 5 |

Other than these components, other solvents known to those skilled in the art suitable for use in the present invention can be used to prepare the liquid formulation, and combinations thereof, including but not limited to alcohols such as but not limited to (methyl, ethyl, butyl, propyl, isopropyl, isopropyl myristate, etc.), glycols such as, but not limited to (propylene, polyethylene, glycerin, etc.) mineral oils, vegetable oils, and others.

Example 2

Figure 2:
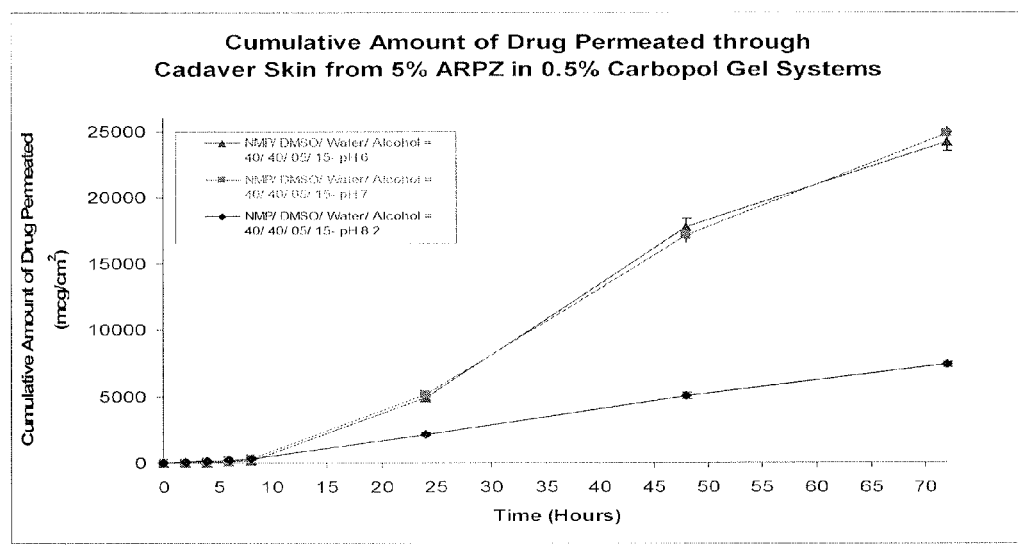
FIG. 2 is a chart showing the Cumulative Amount of 5% ARPZ Permeated through Cadaver Skin from 0.5% Carbopol Gel System.

The effect of gelling agents and their concentration on the permeation of ARPZ through artificial membranes and human cadaver skin was evaluated and two characteristic graphs are shown in FIGS. 1 & 2. The optimal desired composition of ARPZ gel formulation contains 0.5% W/V Carbopol 971. ARPZ can be gelled by gelling agents, including but not limited to, natural polymers (such as agar, alginic acid and derivatives, cassia tora, collagen, gelatin, gellum gum, guar gum, pectin, potassium, or sodium carageenan, tragacanth, xanthan, etc), semisynthetic polymers (such as methylcellulose, carbosymethylcellulose, hydroxypropylcellulose, hydroxypropylmethylcellulose, etc.) synthetic polymers (such as carboxyvinyl polymers or carbomers: carbopol 940, carbopol 934, carbopol 971, poloxamer, polyacrylamide, polyvinyl alcohol, polyethylene, and its co-polymers etc), and clays (such as silicates, etc). In addition, other than cellulose membranes, ARPZ can be evaluated with other artificial membranes including but not limited to silicone membranes (polydimethylsiloxane), liposome-coated membranes, solid-supported liquid membranes, lecithin organogel membranes and others. Besides the gel formulations of ARPZ, other dosage forms include, but are not limited to, ointments, creams, emulsions, liposomes, etc. may be used.

Example 3

Figure 3:
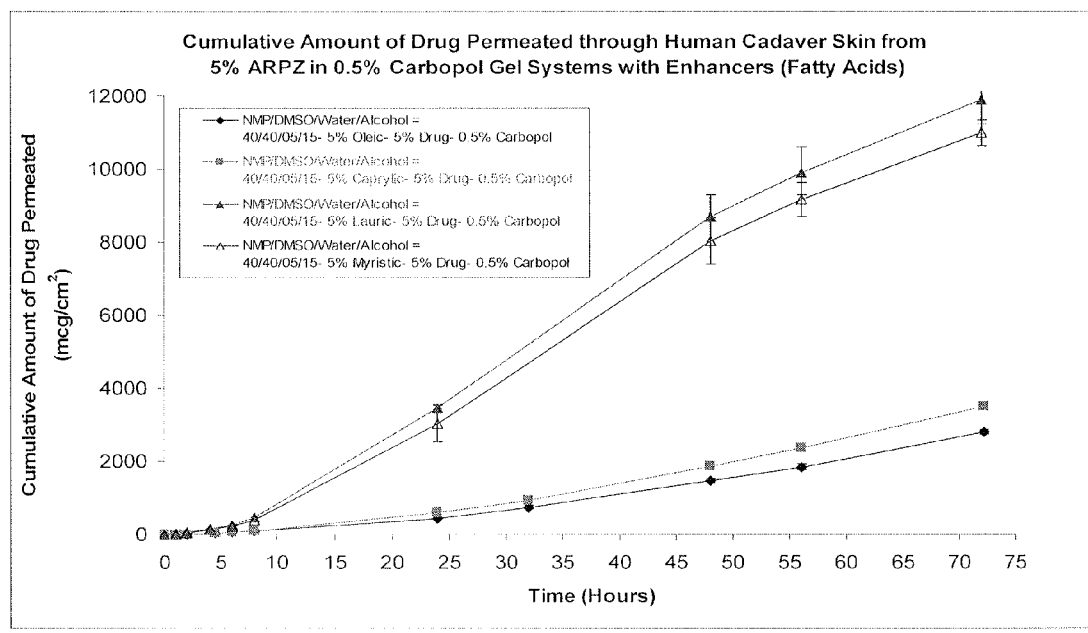
FIG. 3 is a chart showing the Cumulative Amount of Drug Permeated through Human Cadaver Skin from 5% ARPZ in 0.5% Carbopol Gel Systems with Enhancers (Fatty Acids).

The effect of enhancers on the flux of ARPZ through human cadaver skin was evaluated and is shown in FIG. 3. The desired optimum composition of ARPZ gel formulation contained Lauric and Myristc acid. Apart from Lauric and Myristc acid enhancer, the ARPZ transdermal delivery can be influenced by enhancers including but not limited to water, sulfoxides, and similar chemicals, dimethylsulfoxide (DMSO), dimethylacetamide (DMAC), dimethylformamide (DMF), decymethylsulfoxide (DCMS) etc, azone, pyrrolidones N-methyl-2-pyrrolidone (NMP), 2-pyrrolidon (2p), etc., fatty acids esters (butyl ethanoate, ethyl ethanoate, ethyl oleate, isopropyl myristate, isopropyl palmiate, methyl ethanolate, etc.), fatty acids (capric, caprylic, lauric, oleic, myristic, linoleic, stearic, palmitic etc), alcohols, fatty alcohols and glycols (nathanol, dodecanol, propylene glycols, glycerol etc), urea, essential oils, terpene and terpenoids (limonene, thymol, cineole etc), liposomes, niosomes, transferomes, ethanosomes, etc.

Example 4

The effects of pH on the permeation of ARPZ through human cadaver skin were evaluated and a characteristic graph is shown in FIG. 2. The preferred optimum composition of ARPZ gel transdermal formulation had a pH in the range of approximately 6 to 7. Other than these optimal pH values, the ARPZ transdermal delivery may be influenced by pH values outside of the preferred range, but to a lesser extent. Thus, the present invention may still be achieved outside of the preferred pH range of approximately 6 to 7, depending upon the circumstances of use.

The systems of this discovery can deliver ARPZ at a flux between 50 mcg/ch-2.h and 800 mcg/ch-2.h, which can produce the required therapeutic ARPZ blood levels. Flux rate can be changed by modifying such parameters as ARPZ initial concentration, surface area of the patch, pH of the formulation, vehicle composition, enhancer type and composition, etc., in accordance with the teachings of the present invention.

Optimum therapeutic outcome requires not only a proper drug selection but also an effective drug delivery. Psychotropic drug compliance of rigorous regular medication schedules is of great importance. In many instances, oral administration of psychotropic agents is considered a less than optimal delivery system due to patient non-compliance[5]. Transdermal delivery of psychotropic drugs, especially with prolonged duration of action, would be valuable in increasing medication compliance, especially in the geriatric population. Further, potential advantages of ARPZ transdermal delivery are as follows: lack of hepatic first pass effect; eliminating the potential for over- or under-dosing; allowing the flexibility of terminating the drug administration by simply removing the patch; providing a simplified therapeutic regimen, thereby assisting medication compliance in the geriatric population.

Example 5

A transdermal composition of Aripiprazole is shown below:

| ARPZ | 2% |
| --- | --- |
| DMSO | 25% |
| NMP | 10% |
| Isopropylalcohol (IPA) | 5% |
| Ethyl Alcohol | 40% |
| PEG 400 | 15% |
| Carbopol 971P | 0.5% |
| HCl | q.s. to pH 6-7 |
| WATER | q.s. to 100% |

Example 6

A transdermal composition of Aripiprazole is shown below:

| ARPZ | 7% |
| --- | --- |
| Carbopol | 5% |
| DMSO | 40% |
| Ethanol | 25% |
| Lactic acid | 5% |
| NMP | 1.75% |
| Oleic acid | 4% |
| PG | 7.25% |
| Water | 5% |

Example 7

A transdermal composition of Aripiprazole is shown below:

| ARPZ | 7% |
| --- | --- |
| Klucel | 2% |
| DMSO | 40% |
| Ethanol | 25% |
| Lactic acid | 5% |
| NMP | 1.75% |
| Oleic acid | 4% |
| PG | 10.25% |
| Water | 5% |

Example 8

A transdermal composition of Aripiprazole is shown below:

| ARPZ | 7% |
| --- | --- |
| Klucel | 4% |
| DMSO | 5% |
| Ethanol | 5% |
| IPM | 1.5% |
| Oleic acid | 23% |
| Lactic acid | 6% |
| PG | 23.5% |
| PEG | 20% |
| Glycerin | 5% |

Example 9

A transdermal composition of Aripiprazole is shown below:

| ARPZ | 7% |
| --- | --- |
| DMSO | 40% |
| NMP | 1.75% |
| PG | 10.25% |
| Ethanol | 16% |
| Lactic acid | 5% |
| Terpineol | 10% |
| Oleic acid | 2% |
| Water | 5% |
| Carbopol | 3% |

Example 10

A transdermal composition of Aripiprazole is shown below:

| ARPZ | 7% |
|---|---|
| DMSO | 40% |
| NMP | 1.75% |
| PG | 9.25% |
| Ethanol | 25% |
| Lactic acid | 5% |
| Oleyl alcohol | 4% |
| Water | 5% |
| Carbopol | 3% |

While the invention has been described in detail and with reference to specific examples thereof, it will be apparent to one skilled in the art that various changes and modifications can be made therein without departing from the spirit and scope thereof.

REFERENCES

1. Inoue, T., Domae, M., Yamada, K., and Furukawa, T. Effects of the novel antipsychotic agent 7-([4-2,3-dichlorophenylo-1-piperazinyl]b Neuroutyloxyo-3,4-dihydro2 (1H)-quinolinone (OPC-14597) on prolactin release from the rat anterior pituitary. J. Pharmacol. Exp. Ther. 1996; 277(1):137-143.
2. Burris, K. D., Moiski, T. F., Ryan, E., Xu, C., Tottori, K., Kikuchi, T., Yocca, F. D, and Molinoff, P. B. Aripiprazole is a high affinity partial agonist at human D2 dopamine receptors. Int. J. Neuropsychopharmacol. 2000; 3(Suppl. 1), S129.
3. Petrie, J. L., Saha, A. R., and McEvoy, J. P. Aripiprazole, a new atypical antipsychotic: Phase II clinical trial results. Eur. Neuropsychopharm 1997; 7 (Suppl 2): S227.
4. Saha, A. R., McQuade, R., Carson, W. H., Ali, M., W., Durbar, G. C., and Ingenito, G. Efficacy and safety of Aripiprazole and Risperidone vs. Placebo in patients with schizophrenia and schizoaffective disorder. World J. Biol Psych 2001; 2 (Suppl 1): 305S.
5. Geeta, A., Sanju, D., Psychotropic Drugs and Transdermal Delivery. An Overview. Int. J. of Pharma and Bio Science, 2001; V 1(2).

What is claimed is:

1. A transdermal pharmaceutical composition comprising aripiprazole about 7%, Carbopol about 5%, DMSO about 40%, Ethanol about 25%, Lactic acid about 5%, N-methyl-2-pyrrolidone (NMP) about 1.75%, Oleic acid about 4%, propylene glycol (PG) about 7.25%, and q.s. water.
2. The transdermal pharmaceutical composition of claim 1 wherein the aripiprazole is in a gel or liquid form.
3. The transdermal pharmaceutical composition of claim 1 wherein the pH of the composition is approximately 6 to 7.
4. A transdermal pharmaceutical composition comprising aripiprazole about 7%, Klucel (hydroxypropylcellulose (HPC)) about 2%, DMSO about 40%, Ethanol about 25%, Lactic acid about 5%, N-methyl-2-pyrrolidone (NMP) about 1.75%, Oleic acid about 4%, propylene glycol about 10.25%, and q.s. water.
5. The transdermal pharmaceutical composition of claim 4 wherein the aripiprazole is in a gel or liquid form.
6. The transdermal pharmaceutical composition of claim 4 wherein the pH of the composition is approximately 6 to 7.
7. A transdermal pharmaceutical composition comprising aripiprazole about 7%, Klucel (hydroxypropylcellulose (HPC)) about 4%, DMSO about 5%, Ethanol about 5%, isopropyl myristate (IPM) about 1.5%, Oleic acid about 23%, Lactic acid about 6%, PG about 23.5%, Polyethylene glycol (PEG)—20%, and Glycerin about 5%.
8. The transdermal pharmaceutical composition of claim 7 wherein the aripirazole is in a gel or liquid form.
9. The transdermal pharmaceutical composition of claim 7 wherein the pH of the composition is approximately 6 to 7.
10. A transdermal pharmaceutical composition comprising aripiprazole about 7%, DMSO about 40%, N-methyl-2-pyrrolidone (NMP) about 1.75%, propylene glycol (PG)—10.25%, Ethanol about 16%, Lactic acid about 5%, Terpineol about 10%, Oleic acid about 2%, Water about 5%, and Carbopol about 3%.
11. The transdermal pharmaceutical composition of claim 10 wherein the aripiprazole is in a gel or liquid form.
12. The transdermal pharmaceutical composition of claim 10 wherein the pH of the composition is approximately 6 to 7.
13. A transdermal pharmaceutical composition comprising aripiprazole about 7%, DMSO about 40%, N-methyl-2-pyrrolidone (NMP) about 1.75%, propylene glycol (PG) about 9.25%, Ethanol about 25%, Lactic acid about 5%, Oleyl alcohol about 4%, Water about 5%, and Carbopol about 3%.
14. The transdermal pharmaceutical composition of claim 13 wherein the aripiprazole is in a gel or liquid form.
15. The transdermal pharmaceutical composition of claim 13 wherein the pH of the composition is approximately 6 to 7.
16. A method of treating schizophrenia in patient in need of such treatment comprising:
    selecting a patient in need of treatment for schizophrenia;
    administering the pharmaceutical composition of claim 1, thereby treating schizophrenia.

* * * * *